(12) United States Patent
Kahn et al.

(10) Patent No.: US 12,350,442 B2
(45) Date of Patent: Jul. 8, 2025

(54) SLEEP MONITORING AND SLEEP AID USAGE

(71) Applicant: Huawei Technologies Co., Ltd., Shenzhen (CN)

(72) Inventors: Philippe Richard Kahn, Santa Cruz, CA (US); Arthur Kinsolving, Santa Cruz, CA (US)

(73) Assignee: Huawei Technologies Co., Ltd., Shenzhen (CN)

( * ) Notice: Subject to any disclaimer, the term of this patent is extended or adjusted under 35 U.S.C. 154(b) by 1087 days.

(21) Appl. No.: 17/308,709

(22) Filed: May 5, 2021

(65) Prior Publication Data

US 2021/0402133 A1 Dec. 30, 2021

Related U.S. Application Data (63) Continuation of application No. 16/274,259, filed on Feb. 13, 2019, now Pat. No. 11,116,934, which is a continuation of application No. 15/333,180, filed on Oct. 24, 2016, now Pat. No. 10,207,075, which is a continuation of application No. 13/842,618, filed on Mar. 15, 2013, now Pat. No. 9,474,876.

(Continued)

(51) Int. Cl.
*A61M 21/02* (2006.01)
*A61B 5/00* (2006.01)
*A61M 21/00* (2006.01)

(52) U.S. Cl.
CPC .......... *A61M 21/02* (2013.01); *A61B 5/4812* (2013.01); *A61M 2021/0027* (2013.01); *A61M 2021/0066* (2013.01); *A61M 2021/0077* (2013.01); *A61M 2205/332* (2013.01); *A61M 2205/3553* (2013.01); *A61M 2205/3569* (2013.01); *A61M 2205/3592* (2013.01); *A61M 2205/50* (2013.01); *A61M 2205/505* (2013.01); *A61M 2210/083* (2013.01); *A61M 2230/06* (2013.01);

(Continued)

(58) Field of Classification Search
CPC .......................................... A61B 5/4806–4815
See application file for complete search history.

(56) References Cited

U.S. PATENT DOCUMENTS

| 3,798,889 A | 3/1974 | Chadwick |
| 4,228,806 A | 10/1980 | Lidow |

(Continued)

FOREIGN PATENT DOCUMENTS

| AU | 2003203967 | 11/2004 |
| DE | 19642316 A1 | 4/1998 |

(Continued)

OTHER PUBLICATIONS

U.S. Appl. No. 16/274,259, filed Feb. 13, 2019.

(Continued)

*Primary Examiner* — Thaddeus B Cox
(74) *Attorney, Agent, or Firm* — Leydig, Voit & Mayer, Ltd.

(57) ABSTRACT

A method and apparatus to improve sleep aid efficacy are provided. The method comprises monitoring the sleeping patterns of a user utilizing a non-intrusive sleep monitoring device. The method further correlates the user's sleep quality and sleep quantity with use of the sleep aid. In one embodiment, the method adjusts the sleep aid based on the sleep statistics. The efficacy of sleep aids is increased by monitoring user's sleep patterns continuously.

12 Claims, 9 Drawing Sheets

Related U.S. Application Data (60) Provisional application No. 61/737,717, filed on Dec. 14, 2012.

(52) U.S. Cl.
CPC ..... *A61M 2230/10* (2013.01); *A61M 2230/18* (2013.01); *A61M 2230/50* (2013.01)

(56) References Cited

U.S. PATENT DOCUMENTS

| | | | |
|---|---|---|---|
| 4,297,685 | A | 10/1981 | Brainard, II |
| 4,573,804 | A | 3/1986 | Kavoussi et al. |
| 4,858,609 | A | 8/1989 | Cole |
| 5,008,865 | A | 4/1991 | Shaffer et al. |
| 5,335,657 | A | 8/1994 | Terry, Jr. et al. |
| 5,458,105 | A | 10/1995 | Taylor et al. |
| 5,928,133 | A | 7/1999 | Halyak |
| 6,239,706 | B1 | 5/2001 | Yoshiike et al. |
| 6,350,275 | B1 | 2/2002 | Vreman et al. |
| 6,361,508 | B1 | 3/2002 | Johnson et al. |
| 6,468,234 | B1 | 10/2002 | Van Der Loos et al. |
| 6,547,728 | B1 | 4/2003 | Cornuejols |
| 6,556,222 | B1 | 4/2003 | Narayanaswami |
| 6,834,436 | B2 | 12/2004 | Townsend et al. |
| 6,888,779 | B2 | 5/2005 | Mollicone et al. |
| 6,928,031 | B1 | 8/2005 | Kanevsky et al. |
| 7,106,662 | B1 | 9/2006 | Acker, Jr. |
| 7,280,439 | B1 | 10/2007 | Shaddox |
| 7,366,572 | B2 | 4/2008 | Heruth et al. |
| 7,572,225 | B2 | 8/2009 | Stahmann et al. |
| 7,914,468 | B2 | 3/2011 | Shalon et al. |
| 8,179,270 | B2 | 5/2012 | Rai et al. |
| 8,398,546 | B2 | 3/2013 | Pacione et al. |
| 8,475,339 | B2 | 7/2013 | Hwang et al. |
| 8,680,974 | B2 | 3/2014 | Meiertoberens et al. |
| 8,738,925 | B1 | 5/2014 | Park et al. |
| 8,892,036 | B1 | 11/2014 | Causey et al. |
| 8,942,719 | B1 | 1/2015 | Hyde et al. |
| 9,474,876 | B1 | 10/2016 | Kahn et al. |
| 9,594,354 | B1 | 3/2017 | Kahn et al. |
| 10,207,075 | B1 | 2/2019 | Kahn et al. |
| 2002/0080035 | A1 | 6/2002 | Youdenko |
| 2003/0095476 | A1 | 5/2003 | Mollicone et al. |
| 2003/0204412 | A1 | 10/2003 | Brier |
| 2003/0231495 | A1 | 12/2003 | Searfoss, III |
| 2004/0034289 | A1 | 2/2004 | Teller et al. |
| 2004/0039254 | A1* | 2/2004 | Stivoric ............... A61B 5/1118 600/300 |
| 2004/0049132 | A1 | 3/2004 | Barron et al. |
| 2004/0133081 | A1 | 7/2004 | Teller et al. |
| 2004/0218472 | A1 | 11/2004 | Narayanaswami et al. |
| 2005/0012622 | A1 | 1/2005 | Sutton |
| 2005/0075116 | A1 | 4/2005 | Laird et al. |
| 2005/0143617 | A1 | 6/2005 | Auphan |
| 2005/0154330 | A1 | 7/2005 | Loree, IV |
| 2005/0190065 | A1 | 9/2005 | Ronnholm |
| 2005/0237479 | A1 | 10/2005 | Rose |
| 2005/0245793 | A1 | 11/2005 | Hilton et al. |
| 2005/0288904 | A1 | 12/2005 | Warrior et al. |
| 2006/0025299 | A1 | 2/2006 | Miller et al. |
| 2006/0064037 | A1 | 3/2006 | Shalon et al. |
| 2006/0252999 | A1 | 11/2006 | Devaul et al. |
| 2006/0266356 | A1 | 11/2006 | Sotos et al. |
| 2006/0293602 | A1 | 12/2006 | Clark |
| 2006/0293608 | A1 | 12/2006 | Rothman et al. |
| 2007/0016091 | A1 | 1/2007 | Butt et al. |
| 2007/0016095 | A1 | 1/2007 | Low et al. |
| 2007/0191692 | A1 | 8/2007 | Hsu et al. |
| 2007/0251997 | A1 | 11/2007 | Brown et al. |
| 2007/0287930 | A1 | 12/2007 | Sutton |
| 2008/0062818 | A1 | 3/2008 | Plancon et al. |
| 2008/0191885 | A1 | 8/2008 | Loree, IV et al. |
| 2008/0234785 | A1 | 9/2008 | Nakayama et al. |
| 2009/0030767 | A1 | 1/2009 | Morris et al. |
| 2009/0048540 | A1 | 2/2009 | Otto et al. |
| 2009/0069644 | A1 | 3/2009 | Hsu et al. |
| 2009/0082699 | A1 | 3/2009 | Bang et al. |
| 2009/0105785 | A1 | 4/2009 | Wei et al. |
| 2009/0128487 | A1 | 5/2009 | Langereis et al. |
| 2009/0143636 | A1 | 6/2009 | Mullen et al. |
| 2009/0203970 | A1 | 8/2009 | Fukushima et al. |
| 2009/0207028 | A1 | 8/2009 | Kubey et al. |
| 2009/0227888 | A1 | 9/2009 | Salmi et al. |
| 2009/0264789 | A1 | 10/2009 | Molnar et al. |
| 2010/0010330 | A1 | 1/2010 | Rankers et al. |
| 2010/0061596 | A1 | 3/2010 | Mostafavi et al. |
| 2010/0075807 | A1 | 3/2010 | Hwang et al. |
| 2010/0079291 | A1 | 4/2010 | Kroll et al. |
| 2010/0079294 | A1 | 4/2010 | Rai et al. |
| 2010/0083968 | A1 | 4/2010 | Wondka et al. |
| 2010/0100004 | A1 | 4/2010 | Van Someren |
| 2010/0102971 | A1 | 4/2010 | Virtanen et al. |
| 2010/0152546 | A1 | 6/2010 | Behan et al. |
| 2010/0256512 | A1 | 10/2010 | Sullivan |
| 2010/0331145 | A1 | 12/2010 | Lakovic et al. |
| 2011/0015467 | A1 | 1/2011 | Dothie et al. |
| 2011/0018720 | A1 | 1/2011 | Rai et al. |
| 2011/0058456 | A1 | 3/2011 | Van De Sluis et al. |
| 2011/0160619 | A1 | 6/2011 | Gabara |
| 2011/0199218 | A1 | 8/2011 | Caldwell et al. |
| 2011/0230790 | A1 | 9/2011 | Kozlov |
| 2011/0267196 | A1* | 11/2011 | Hu ....................... A61B 5/4815 340/575 |
| 2011/0295083 | A1 | 12/2011 | Doelling et al. |
| 2012/0083715 | A1 | 4/2012 | Yuen et al. |
| 2012/0243379 | A1 | 9/2012 | Balli |
| 2012/0253220 | A1 | 10/2012 | Rai et al. |
| 2012/0296156 | A1* | 11/2012 | Auphan ............... A61M 21/02 600/26 |
| 2013/0018284 | A1 | 1/2013 | Kahn et al. |
| 2013/0023214 | A1 | 1/2013 | Wang et al. |
| 2013/0060306 | A1 | 3/2013 | Colbauch |
| 2013/0286793 | A1 | 10/2013 | Umamoto |
| 2013/0289419 | A1 | 10/2013 | Berezhnyy et al. |
| 2013/0310658 | A1 | 11/2013 | Ricks et al. |
| 2014/0005502 | A1 | 1/2014 | Klap et al. |
| 2014/0051938 | A1 | 2/2014 | Goldstein et al. |
| 2014/0058703 | A1* | 2/2014 | Kimishima .......... G06Q 10/109 702/177 |
| 2014/0085077 | A1 | 3/2014 | Luna et al. |
| 2014/0135955 | A1 | 5/2014 | Burroughs |
| 2014/0200691 | A1 | 7/2014 | Lee et al. |
| 2014/0207292 | A1 | 7/2014 | Ramagem et al. |
| 2014/0219064 | A1 | 8/2014 | Filipi et al. |
| 2014/0232558 | A1 | 8/2014 | Park et al. |
| 2014/0256227 | A1 | 9/2014 | Aoki et al. |
| 2014/0288878 | A1 | 9/2014 | Donaldson |
| 2014/0347366 | A1* | 11/2014 | Emori ..................... A61B 5/742 345/440 |
| 2015/0098309 | A1 | 4/2015 | Adams et al. |
| 2015/0148871 | A1 | 5/2015 | Maxik et al. |
| 2015/0178362 | A1 | 6/2015 | Wheeler |
| 2015/0190086 | A1 | 7/2015 | Chan et al. |
| 2015/0265903 | A1 | 9/2015 | Kolen et al. |
| 2017/0003666 | A1 | 1/2017 | Nunn et al. |

FOREIGN PATENT DOCUMENTS

| | | |
|---|---|---|
| EP | 1139187 B1 | 10/2001 |
| JP | 8160172 | 6/1996 |
| KR | 1020009085403 | 6/2011 |
| KR | 1020100022217 | 3/2012 |
| WO | 9302731 | 2/1993 |
| WO | 2008038288 A3 | 5/2009 |
| WO | 2009099292 A2 | 8/2009 |
| WO | 2011141840 A1 | 11/2011 |
| WO | WO-2012108736 A2 * | 8/2012 ............ A61M 21/02 |

OTHER PUBLICATIONS

U.S. Appl. No. 15/333,180, filed Oct. 24, 2016.
U.S. Appl. No. 13/842,618, filed Mar. 15, 2013.

(56) References Cited

OTHER PUBLICATIONS

Slow Wave Sleep, <en.wikipedia.org/wiki/Slow-wave.sub.-sleep>, Last Modified Jul. 22, 2012, 4 pages.
Actigraphy, From Wikipedia, the free encyclopedia, downloaded at: http://en.wikipedia.org/wiki/Actigraphy on Apr. 24, 2014, 4 pages.
David F. Dinges, <en.wikipedia.org/wiki/David_Dinges>, Last Modified Sep. 12, 2012, 2 pages.
Desai, Rajiv, The Sleep, Archive for Mar. 2011, Dr. Rajiv Desai Blog, Mar. 17, 2011, 46 pages.
Jaines, Kira, "Music to Help You Fall Sleep," <http://www.livestrong.com/article/119802-music-fall-sleep/>, May 10, 2010, 2 pages.
Jetlog Reviewers Guide, <http://wwwjetlog.com/fileadmin/Presse.sub.-us/24x7ReviewersGuide.pdf- >, 2009, 5 pages.
Lichstein, et al., Actigraphy Validation with Insomnia, Sleep, vol. 29, No. 2, 2006, pp. 232-239.
Patel, et al., Validation of Basis Science Advanced Sleep Analysis, Estimation of Sleep Stages and Sleep Duration, Basis Science, San Francisco, CA, Jan. 2014, 6 pages.
Pires, P. D. C. Activity Characterization from Actimetry Sensor Data for Sleep Disorders Diagnosis, Universidade Tecnica de Lisboa, Sep. 2008, 60 pages.
Pollak, et al., How Accurately Does Wrist Actigraphy Identify the States of Sleep and Wakefulness?, Actigraphy and Sleep, Sleep, vol. 24, No. 8, 2001, pp. 957-965.
Sound-Remedies.com: Sonic Solutions for Health, Learning & Productivity, <http://www.sound-remedies.com/ammusforslee.html>, Accessed May 23, 2013, 2 pages.
Sunseri, Maria, et al, "The SenseWear (TM) Armband as a Sleep Detection Device," <http://sensewear.bodymedia.com/SenseWear-Studies/SW-Whitepapers/The-SenseWear-armband-as-a-Sleep-Detection-Device>, 2005, 9 pages.

\* cited by examiner

| SLEEP AID | ADJUSTMENT |
|---|---|
| Prescription pill | Time to take medicine, time to go to sleep, dosage |
| Continuous Administered Medicine | Time to start administration, dosage through time, dosage by current sleep phase |
| Time release medicine | Time to take, time release timing through sleep |
| Sound-based sleep aids | Sounds and sound levels by sleep phase, sleep phase transition |
| Uppers/Downers (caffeine/alcohol) | Time to stop taking, time to start taking, quantity limitations |
| Eye coverings | Usage (may be recommended if waking is by light) |
| Airflow control | Use by sleep phase, phase transition |
| Environmental controls (temperature, light, bed softness) | Changes by sleep phase, phase transition. |
| Tactile Output | Use tactile output to wake, or transition in sleep phase |
| Olfactory Output | Use by sleep phase, and/or sleep transition |
| Other sensory output | Use as needed, sleep phase/transitions |

SLEEP MONITORING AND SLEEP AID USAGE

CROSS-REFERENCE TO RELATED APPLICATIONS

This application is a continuation of U.S. patent application Ser. No. 16/274,259, filed on Feb. 13, 2019, and issued on Sep. 14, 2021, as U.S. Pat. No. 11,116,934, which is a continuation of U.S. patent application Ser. No. 15/333,180, filed on Oct. 24, 2016, and issued on Feb. 19, 2019, as U.S. Pat. No. 10,207,075 which is a continuation of U.S. patent application Ser. No. 13/842,618, filed on Mar. 15, 2013, and issued on Oct. 25, 2016, as U.S. Pat. No. 9,474,876, which claims priority to U.S. Provisional Application 61/737,717 filed on Dec. 14, 2012, and incorporates all of the above applications in their entirety by reference.

TECHNICAL FIELD

Embodiments of the present invention relate to sleeping, and more particularly to improving the efficacy of sleep aids.

BACKGROUND

Sleep has been found to be vital to human health. It influences everything from concentration, to IQ, to weight. However, a significant number of people have difficulty sleeping. Such difficulty ranges from difficulty getting enough sleep, difficulty falling asleep, difficulty breathing while sleeping, waking up repeatedly, etc. Many people attempt to mediate their difficulty sleeping using various sleep aids, including drugs, breathing machines, eye masks, and other things to improve the ability to sleep.

In some instances, people go into sleep clinics, to diagnose their difficulties, and attempt to get treatment.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

As sleep aids become more commonly used, the efficacy of a sleep aid, and its interaction with the user's particular patterns of sleep are difficult to optimize. While some users can go to a sleep clinic, that is an expensive option. Additionally, being wired up and sleeping in an unfamiliar place may alter a user's sleep patterns. Furthermore, sleep patterns change over time, seasonally, and based on the user's current circumstances. Therefore, a sleep monitoring system is described, which increases the efficacy of sleep aids by monitoring user's sleep patterns continuously, and in one embodiment adjusting the sleep aids used based on real and continuous data.

For example, a user taking a popular sleep aid such as AMBIEN® may find that it helps in falling asleep, but only if the user is in bed within 30 minutes of taking the medicine, but no earlier than 15 minutes after taking the medicine. A sleep monitoring system that can provide an alarm, and ensure that the user gets the most out of this drug, would be useful. For another example, some users have no difficulty falling asleep, but wake frequently through the night. Another type of drug may be recommended to such users. Additional non-drug sleep aids may also be utilized. Such non-drug sleep aids may include breathing machines, music which may have a particular beat pattern, white noise machines, eye masks, temperature adjustments, mattress softness, etc. Additionally, self-medicating with various types of sleep aids, such as caffeine and alcohol, as well as decongestant medications may have effects on the user's sleep pattern.

In one embodiment, a continuously administered drug-based sleep aid may be utilized. The continuous administration may be through a pump, like an insulin pump, or through a time-release capsule, or through other means. The sleep monitoring system may be used to monitor the user's sleep patterns, and automatically adjust the drug, as needed, through the night. The sleep monitoring system may, alternatively, be used to monitor the user's sleep patterns, and provide feedback such that a time-release capsule or similar customized drug dispensing method provides the optimal levels of the sleep aid at the times needed by the user.

The sleep monitoring system's output may also, in one embodiment, be provided to the user and/or doctor or other party. This enables the user/doctor/third party to adjust the use of various sleep aids, and/or add or subtract sleep aids from the user's prescription.

In one embodiment, cumulative data from sleep monitoring systems may also be made available. In one embodiment, this data is abstracted and anonymized. This may be used to adjust sleep aids, based on observed data. In one embodiment, cumulative sleep data may also be used to prove the efficacy of new sleep aids. For example, instead of very limited clinical trials in a sleep clinic, a larger group of people may be provided with the sleep monitoring system, to receive real-life sleep data, from users' normal environments.

Additionally, the sleep monitoring system may, in one embodiment, monitor the user for additional medical conditions. For example, some sleep aids may cause health issues. In one embodiment, the sleep monitoring system includes health monitoring. In one embodiment, the sleep monitoring system integrates with a health monitoring system separately implemented. The combination of the sleep monitoring and health monitoring that can ensure that the user is not having a medical reaction to any sleep aids.

In one embodiment, the sleep monitoring system further includes or integrates with an activity monitoring system. It is well known that a user's activities and actions through the day influence his or her sleep. Therefore, having additional daily activity monitoring available may further improve the efficacy and use of sleep aids.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1:
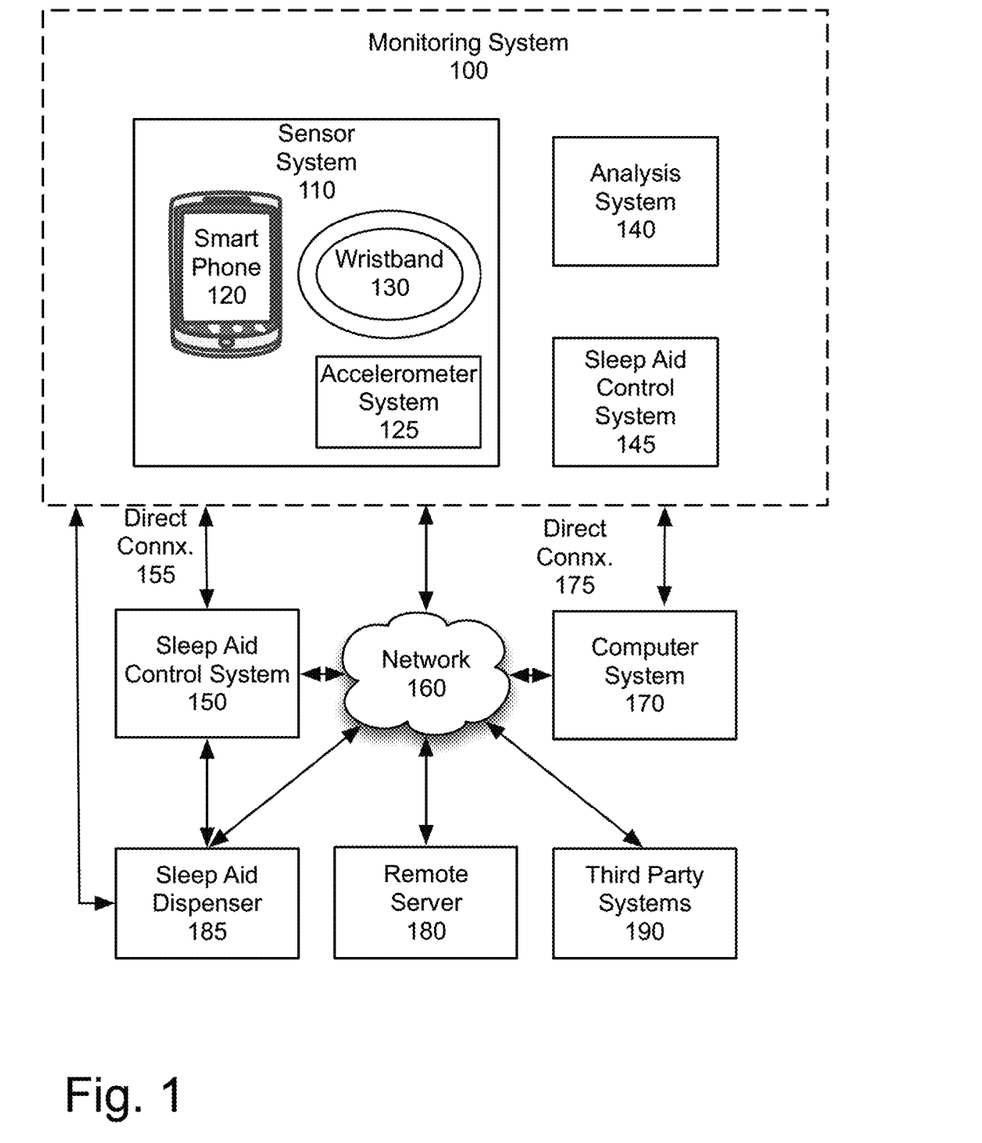
FIG. 1 is a network diagram illustrating one embodiment of the elements that may be part of the system and their relationships.

FIG. 1 is a network diagram illustrating one embodiment of the elements that may be part of the system and their relationships. The system, in one embodiment, includes a monitoring system 100. The monitoring system 100 includes sensor system 110. The sensor system 110 may be embodied in a body-worn device such as a wristband 130, a human carried device such as a smart phone 180 or accelerometer system 185. In one embodiment, the sensor system 110 may be implemented in a sleep-only device such as an armband or pillow. Sensor system 110 may be implemented in a combination of various types of sensors, which can be utilized to detect a user's sleep patterns including headsets, cameras, goggles, arm bands, or other mechanisms. In one embodiment, some of the sensors may be in one system, while others are in another system. For example, activity monitor may be implemented in a wristband 130, while sleep monitor is implemented in a pillow, etc.

The monitoring system 100 further includes analysis system 140. Analysis system utilizes the data from the sensor system 110, to determine the user's sleep phases, and the interaction of the applicable sleep aids with the user's sleep quality and quantity.

In one embodiment, the monitoring system 100 includes a sleep aid control system 145. Sleep aid control system in one embodiment provides real-time adjustment of sleep aids, ranging from medications to environmental conditions, as needed, to ensure a restful sleep for the user. In another embodiment, the sleep aid control system 150 is located outside the monitoring system 100. In one embodiment, the interface between the monitoring system 110 and the sleep aid control system 150 may be through an audio jack interface, a Bluetooth™ or other personal area network interface, or a network interface 160.

In one embodiment, sleep aid dispenser 185 may be coupled to sleep aid control system 150 and/or monitoring system 100. The coupling may be direct, or via network 160 or other means. In one embodiment, the sleep aid dispenser 185 may be incorporated within the monitoring system 100, making a unitary system. In one such embodiment, the only necessary elements of the system are a sensor system that monitors a user's sleep, an analysis system that analyzes the result of the monitoring, and a sleep aid controller/dispenser that controls a relevant sleep aid. In one embodiment, sleep aid control system 150 may interface with, or include, home automation controls.

In one embodiment, the sensing system 100 may communicate with the analysis system 140 through an audio jack interface, a Bluetooth™ or other personal area network interface, or a network interface 160, rather than being implemented in the same device. Network 160 may include one or more of a wireless network (WiFi), cellular network, a local area network, a personal area network (PAN) such as BLUETOOTH™, or another type of wireless connection.

The network 160 may provide access to a computer system 170, remote server 180, and/or Internet data on various third party systems 190. The computer system 170 may provide additional processing, and may, in one embodiment, provide the user with an additional user interface features. In one embodiment, the computer system 170 may be coupled directly to the monitoring system 100, continuously or periodically, via direct connection 175. This could be implemented, in one embodiment, via a Universal Serial Bus (USB), audio input based interface, or other type of wired connection.

In one embodiment, server 180 may provide data to the monitoring system 100. In one embodiment, the monitoring system 100 may also provide information to the server 180. In one embodiment, a remote server 180 may collect data from multiple users, and use cumulative data and statistical analysis to provide predictive recommendations, set default options, and suggest alterations to settings.

In one embodiment, the monitoring system 100 may also couple to network 160 to third party systems 190. Third party systems 190 may provide environmental data to the sleep sensing system 100. Third party systems 190 may also provide sounds to the sleep sensing system 100, as will be described below. In one embodiment, third party system 190 may be a pharmacy or retailer that can provide the option to purchase additional relevant sleep aids, as recommended.

Figure 2A:
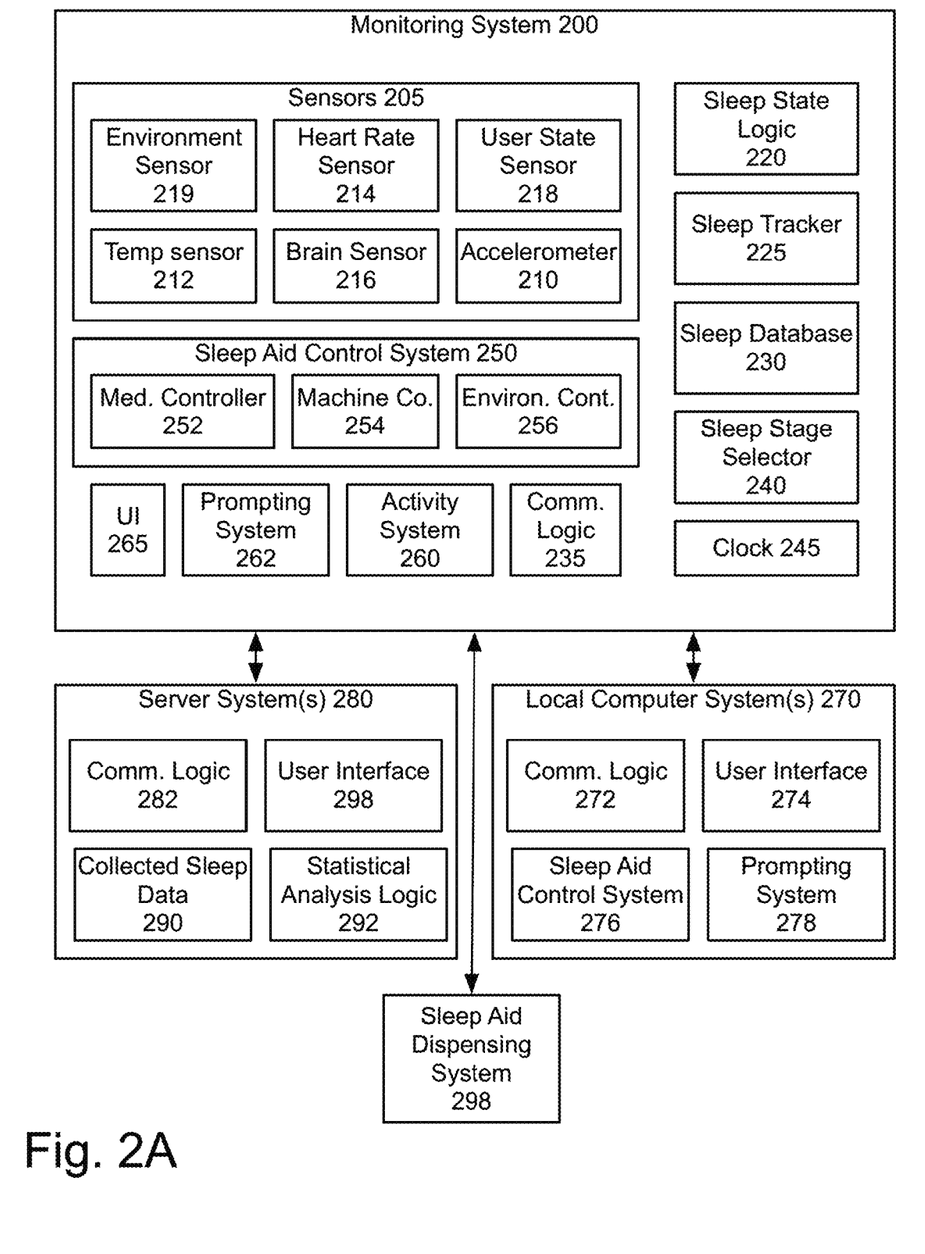
FIG. 2A is a block diagram of one embodiment of the system.

FIG. 2 is a block diagram of one embodiment of the system, including monitoring system 100 and local system 270 as well as server system 280, to which the monitoring system 100 may be coupled directly or via a network connection. In one embodiment, the server system 280 may be a local personal computer, a local server computer, or a remote server system, or a system-accessible website or other source of data.

The monitoring system 200 includes one or more sensors 205. The sensors 205 may include an accelerometer 210, a temperature sensor 212, a heart rate sensor 214. In one embodiment, temperature sensor 212 may include two sensors, one for the user's body temperature and the other for ambient temperature sensing. In one embodiment, sensors that detect brain waves 216 may also be used. In one embodiment, brainwave sensors, cameras to observe eye movement, or other sensors 218 may also monitor the user's state. Additional sensors to monitor the user's state 218, and the user's environment 219 may also be part of the sleep sensing system 100.

Monitoring system 200 further includes sleep state logic 220. Sleep state logic 220 receives data from one or more sensors 205, to determine the user's current sleep state. In one embodiment, sleep states may include awake, light sleep, and deep sleep. In one embodiment, the sleep state may be N1, N2, N3, and REM. In another embodiment, the sleep state may be light sleep, deep sleep, and REM sleep. Other divisions, or further subdivisions, may also be present. In one embodiment, sleep state can be determined by sleep state logic 220 based on the user's micro-movements, body temperature, heart rate, and/or brain function, as determined by sensors 205.

Sleep tracker 225 receives the current sleep state information from sleep state logic 220 and tracks the overall sleep state for the present sleep cycle. Sleep tracker 225 in one embodiment also adds data to a sleep database 230. The sleep database 230 tracks sleep state information longer term. In one embodiment, the information in the sleep database 230 may be used to correlate the use of the sleep aids with sleep patterns, and thus provide predictive modeling for the user. In one embodiment, the data from sleep database 225 may be passed to a computer system 280 using communication logic 235.

The data from sleep tracker 225 and sleep state logic 220 is used by the sleep stage selector 240, in one embodiment, to select the optimal current sleep stage for the user. In one embodiment, data from clock 245 and alarm logic 270 is also used by the sleep stage selector 240. In one embodiment, data from environment sensor 219 may also be used by sleep stage selector 240. In one embodiment, data from computing system(s) 280 may also be used by the sleep stage selector 240.

The optimal next sleep state, as selected by sleep state selector 240 is passed to sleep aid control system 250. In one embodiment, the optimal next sleep state may be the same state as the current sleep state. Sleep aid control system 250 in one embodiment can control one or more of medicine controller 252, machine controller 254, and environmental controller 256. Environmental controller 256 may control the user's environment, such as temperature, sounds, light levels, etc. to either maintain the user in their current sleep state, or transition them to the appropriate optimal next sleep stage. Medicine dispenser 252 may be utilized for the same purpose. In one embodiment, additional machines, may be controlled via machine controller 254. Such machines may include positive airflow machines, in one embodiment. In one embodiment, the medicine dispenser 252 may be a sleep pump that dispenses sleep medications in a time-release fashion, to ensure optimal sleep. In one embodiment, environmental controller 256 may include an interface to a home automation system, or other existing control system that may control the environment.

In one embodiment, the user may enter preferences through user interface 265, or via a user interface 274 on local computing system 270, or user interface 298 on server system 280. Interface 298 may be accessed through a web page or other interface.

In one embodiment, monitoring system 200 includes an activity system 260 monitor the user's activity levels. The user's daily activity can influence the user's sleep quality, and thus the need for sleep aids. Therefore, in one embodiment, the system includes activity system 260, which uses sensor data to analyze the user's daily activity levels. In another embodiment, the activity monitoring sensors may be implemented in a separate device, and its data may be provided to activity system 260.

In one embodiment, prompting system 262 may prompt the user to input his or her sleep aid consumption. The prompting system 262 may also provide prompts to the user, to ensure that the user takes medicines at the appropriate time, and/or goes to sleep at the appropriate time, etc.

The local computer system 270 in one embodiment includes a sleep aid control system 276, to control one or more external sleep aids, which may range from medications, to machines, and to mechanisms. In one embodiment, this element is needed when sleep aid control system 250 is replaced by sleep aid control system 276, or other external methods of controlling sleep aids. Prompting system 278 may also be located in local computer systems 270.

Server system 280, in one embodiment, includes a mechanism to collect sleep data 290, and statistical analysis logic 292. The statistical analysis logic 292 analyzes the abstracted and anonymized data from multiple users. The collective data of these users may be used to generate recommendations, warn of problems, and in one embodiment to enable the use of the system to perform sleep studies.

In one embodiment, statistical analysis logic 292 may adjust sleep aids, or recommend changes, based on observed data. In one embodiment, the statistical analysis results may also be used to prove the efficacy of new sleep aids.

Figure 3:
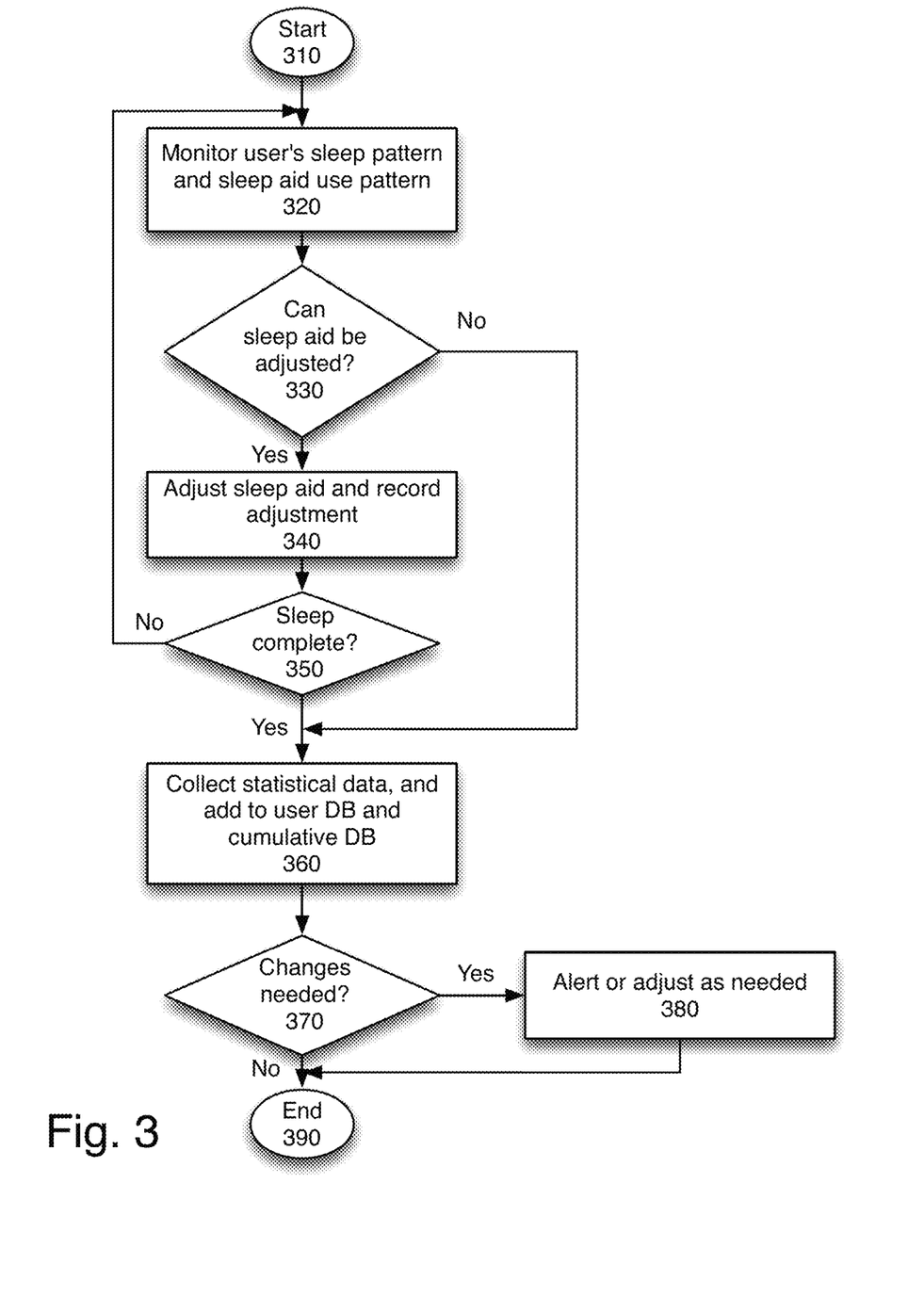
FIG. 3 is an overview flowchart of one embodiment of using the system.

FIG. 3 is an overview flowchart of one embodiment of using the system. The process starts at block 310.

At block 320, the system monitors the user's sleep pattern and sleep aid use patterns and data. In one embodiment, this may be done using multiple sensing devices, as well as user-entered data.

Figure 2B:
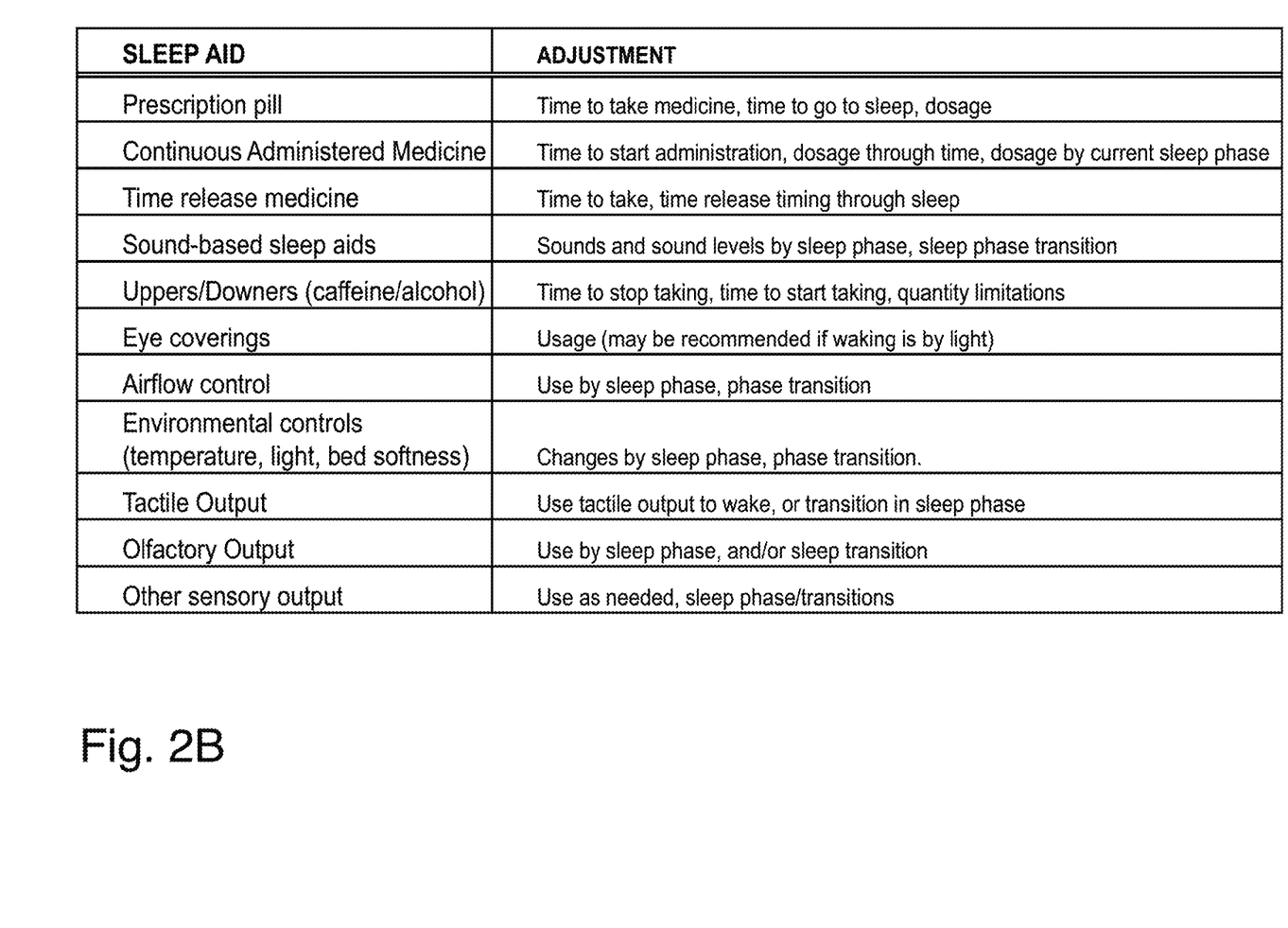
FIG. 2B is a table of one embodiment of a set of adjustments recommended, for various sleep aids, based on observed sleep results.

At block 330, the process determines whether any sleep aids can be adjusted in real-time. If so, at block 340, the sleep aid is adjusted if needed, and any adjustment is recorded. FIG. 2B shows a table of potential adjustments that may be made in real time. Such adjustments include increasing sleep medication, altering local temperature, altering local light levels, altering sound levels, airflow, etc. Of course the set of adjustments shown in FIG. 2B are merely exemplary. A system may have more or fewer controls. In one embodiment, there may be no real-time controls available, and all adjustments may be based on recommending changes to the user, or an appropriate entity such as the user's doctor or health insurance provider.

The process then determines whether sleep is complete, e.g., the user has woken up, at block 350. If the user has not yet woken, the process returns to block 320 to continue monitoring the user's sleep. If the user has woken, the process continues to block 360. If the sleep aid cannot be adjusted, the process continues directly to block 360.

At block 360, statistical data is collected. In one embodiment, the statistical data is added to the user database, and cumulative database. In one embodiment, the statistical data includes user sleep data automatically recorded, relevant sleep aids and any sleep aid adjustments made. In one embodiment, additional data, such as subjective sleep quality, may also be collected from the user and added to the system.

At block 370, the process determines whether the user's sleep aids, or sleep habits, need adjustments. If so, at block 380, these suggested alterations are provided. In one embodiment, the suggested alterations may be provided to the user. Such adjustments may include suggestions to utilize an eye mask, suggestions to add a white noise machine, suggestions to lower the temperature, increase or decrease sleep medication dosage, etc. The process then ends, at block 390. In this way, the user's sleep is monitored, and the sleep aids are adjusted either in real-time if possible, or via adjustments or alerts after the conclusion of sleep.

In one embodiment, this monitoring may be useful as part of a sleep study. A user's sleep patterns may be studied, and adjusted by introducing one or more sleep aids over time. This enables a user to participate in a sleep study in their home environment, and determine the optimal sleep aids to use, to have restful and appropriate sleep.

Figure 4:
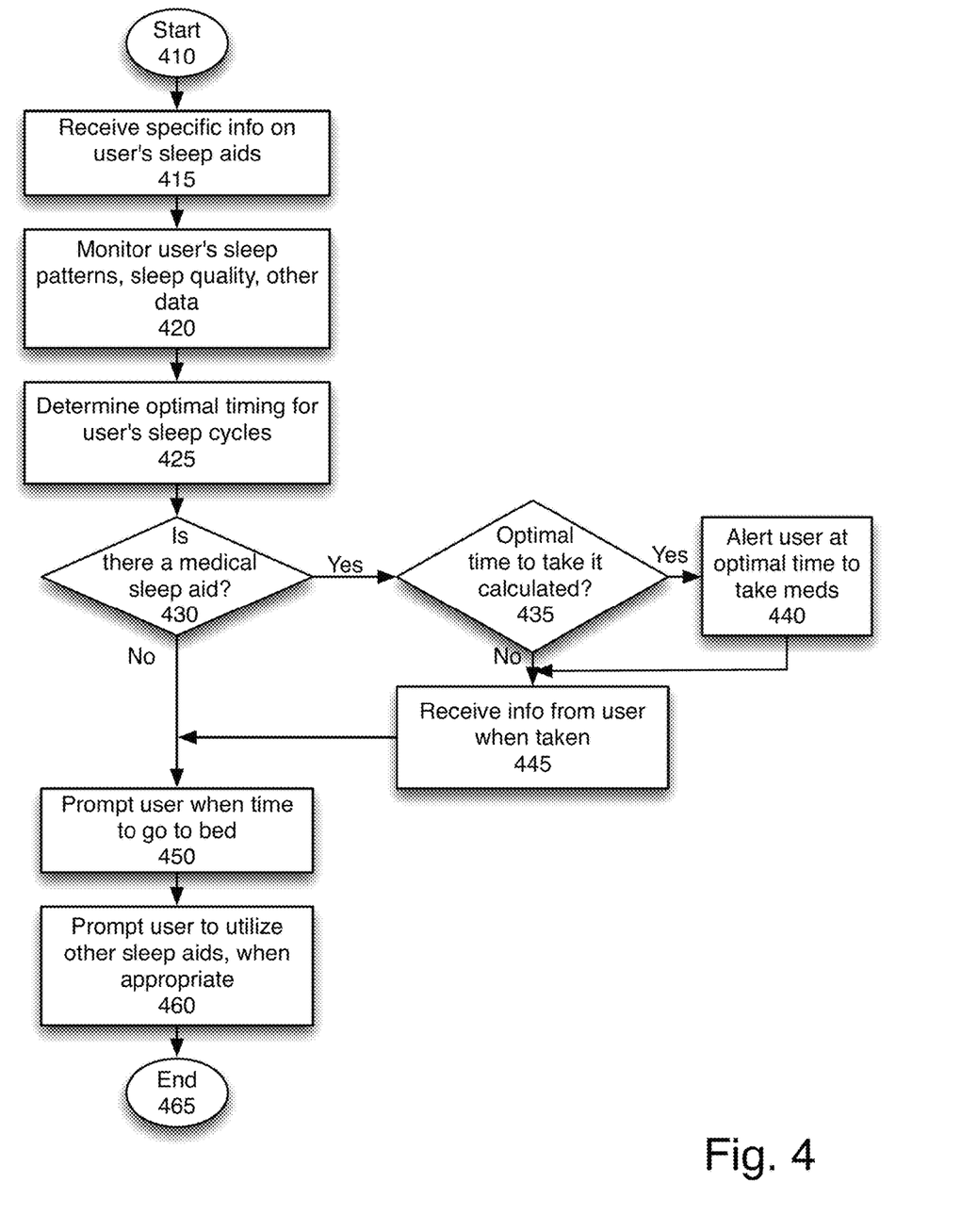
FIG. 4 is a flowchart of one embodiment of communicating with a user in conjunction with initiating sleep.

FIG. 4 is a flowchart of one embodiment of communicating with a user in conjunction with initiating sleep. The process starts at block 410.

At block 415, information is received on the user's sleep aids. In one embodiment, the user may be prompted with a list of sleep aids that may be available. In one embodiment, sleep aid data may be received, with the user's authorization, from a doctor or other prescriber. Sleep aids range from medicines such as AMBIEN® to environmental adjustments such as wearing an eye mask or using a white noise machine, or non-prescription drugs such as caffeine and alcohol. In one embodiment, the user is prompted to enter the sleep aids used, their dosage and frequency. In one embodiment, some or all of this data may be obtained from medical records released by the user to the system. In one embodiment, some or all of this data may be obtained by other means, such as based on photographs provided by the user.

At block 420, the user's sleep patterns, sleep quality, and other sleep data is monitored. In one embodiment, a number of sleep sessions are observed before any personalized recommendations are provided to the user. However, in one embodiment, default "standard" recommendations may be available based on data associated with medications, research, or collected statistical data.

At block 425, the system determines the optimal timing for the user's sleep cycles. This is based on the user's historical behavior, as well as known information about the amount of sleep a person fitting the user's profile needs.

At block 430, the process determines whether there is a medical sleep aid. If so, at block 435, the process determines whether the system has sufficient data to have calculated an optimal time to take the sleep aid. Many sleep aids have a limited time during which they work best, or a limited duration. Therefore, having a user take a sleep aid too early, such that during the most effective period the user is unlikely to be in bed, is negative. Recommending the optimal time to take the sleep aid can be important. If such data is available, at block 440, the user is alerted to take the medication at the optimal time.

The system then monitors for the user taking the sleep aid, whether or not the user was alerted, at block 445. In one embodiment, the user manually enters the time when the sleeping aid was taken.

At block 450, the user is prompted when it is time to go to bed. This occurs, in one embodiment, whether or not there is a medical sleep aid.

At block 460, the user is prompted to set other sleep aids, when available. As noted, the system is aware of the available sleep aids. In one embodiment, the prompting may include reminders such as "close the blinds and turn on the white noise machine." The process then ends, at block 465, as the system switches to monitoring the user's sleep patterns.

Figure 5:
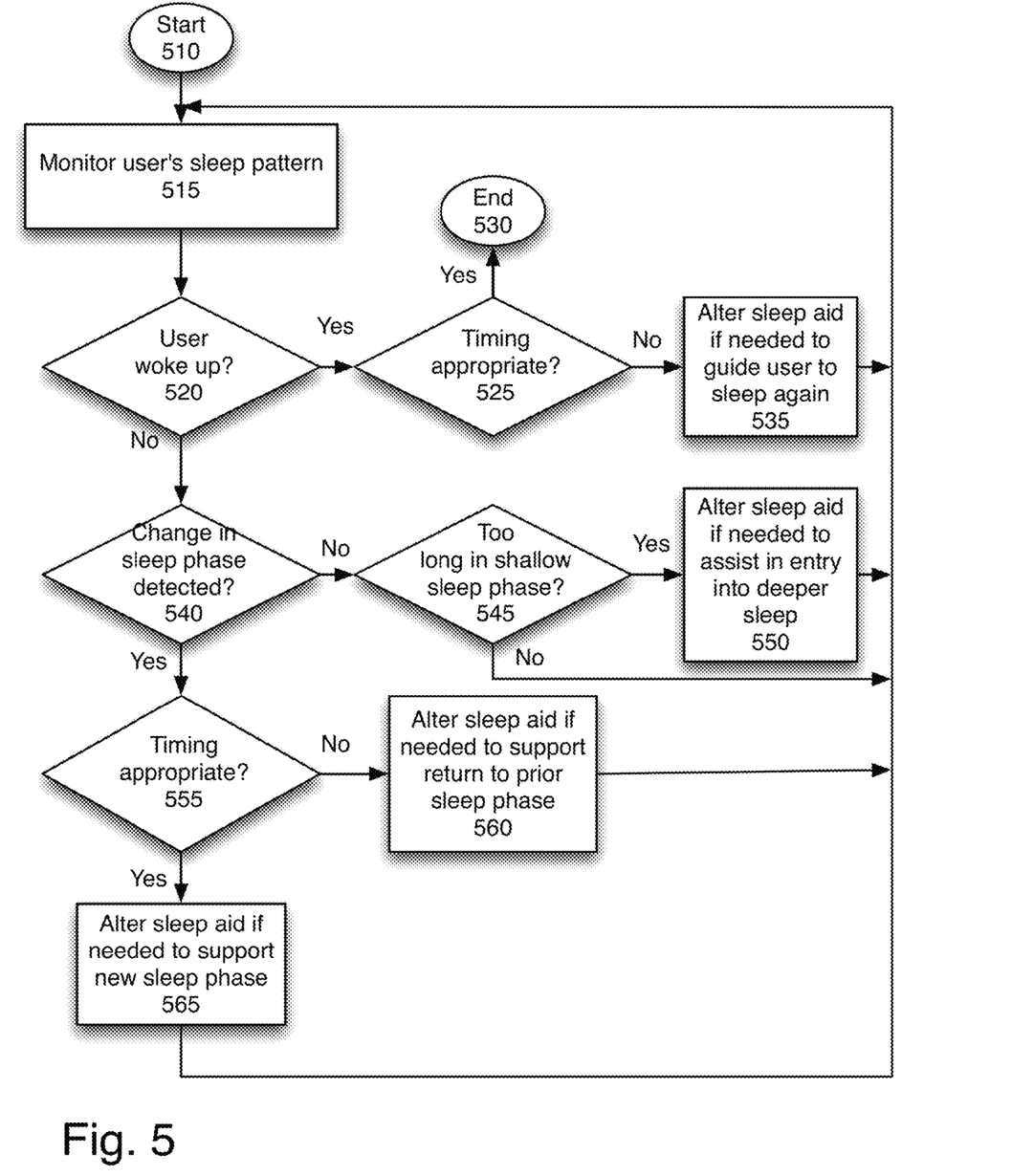
FIG. 5 is a flowchart of one embodiment of adjusting a sleep aid during sleep.

FIG. 5 is a flowchart of one embodiment of adjusting a sleep aid during sleep. The process starts at block 510. This process applies only when there are one or more sleep aids that are adjustable in real time. Such sleep aids may include room temperature, sounds, light levels, bed softness, and other environmental factors. In one embodiment, such factors may also include adjusting the dispensing of sleep medicines. Sleep medicines such as AMBIEN® and others may be provided in a liquid form, which may be dispensed through a mechanism such as a pump. Drug pumps release controlled doses of medication, such as pain medication. Such drug pumps, in one embodiment, can be utilized to release controlled doses of sleep medication. Because the dosage is precisely correlated with the user's sleep state and thus need for medication, the overall drug consumption is decreased. This also eliminates many of the side effects of such medications, which are the result of a mismatch between sleep state and drug levels.

At block 515, the user's sleep pattern is monitored. At block 520, the process determines whether the user woke up. In one embodiment, waking up may include entering a very light sleep phase, in which the user is in the "half-asleep" state. If so, at block 525, the process determines whether the timing is appropriate for waking. If so, the process ends at block 530. As noted above, the user's statistical data would then be analyzed, and further adjustments made. But the real-time adjustment terminates when the user wakes, in one embodiment.

If the timing is found not to be appropriate, at block 535, the sleep aid is altered to guide user to sleep again. In one embodiment, if the sleep aid is medicinal in form, some additional medicine may be added to the user's system, to ensure additional sleep. For another example, it may be that the user is waking in part because the room is too light. If the system has control over blinds, the blinds may be lowered. In one embodiment, if the user is waking as a result of a nightmare—as determined by the pattern of movements—the system may guide the user to full wakefulness, and allow them to return to more restful sleep thereafter. The process then returns to block 515, to continue monitoring the user's sleep pattern.

If the user is not waking up, at block 520, the process determines at block 540 whether a change in sleep phase is detected. If no change in sleep phase is detected, the process determines whether the user is remaining in a too shallow sleep phase for too long. In one general, the most restful and necessary sleep is the deep sleep. Therefore, excessive light sleep is not optimal. If the user is not remaining in light sleep for too long, the process continues to block 515 to continue monitoring.

If the user is found to be too long in shallow sleep, at block 550, the sleep aid is altered to assist in entry into deeper sleep. This may include adjusting medication, adjusting airflow, adjusting temperature, adjusting the soundscape, etc. The process then returns to block 515.

If a change in sleep phase is detected, the process determines whether the change in sleep phase is appropriate. As noted, extended deep sleep is important. Furthermore, a certain amount of lighter sleep is needed because that is time when the user dreams, which is necessary for mental health. If the timing is appropriate at block 565, the process ensures that the current settings for the sleep aid are appropriate to support the transition to the new sleep phase. If needed, the sleep aids may be adjusted at that point. The process then returns to block 515, to continue monitoring.

If the timing is not appropriate, at block 560, the sleep aid may be altered to support return to the prior sleep phase. Again, this may include altering medication, airflow, temperature, bed softness, and other environmental factors.

The exemplary methods shown in FIG. 5 are meant to be exemplary. In one embodiment, the system continuously monitors the current sleep phase, and not just transitions and timing. In one embodiment, other factors such as sleep quality are monitored. For example, the changes in sleep aid may be made in response to the user having a bad dream, not breathing well, waking excessively, etc.

Figure 6:
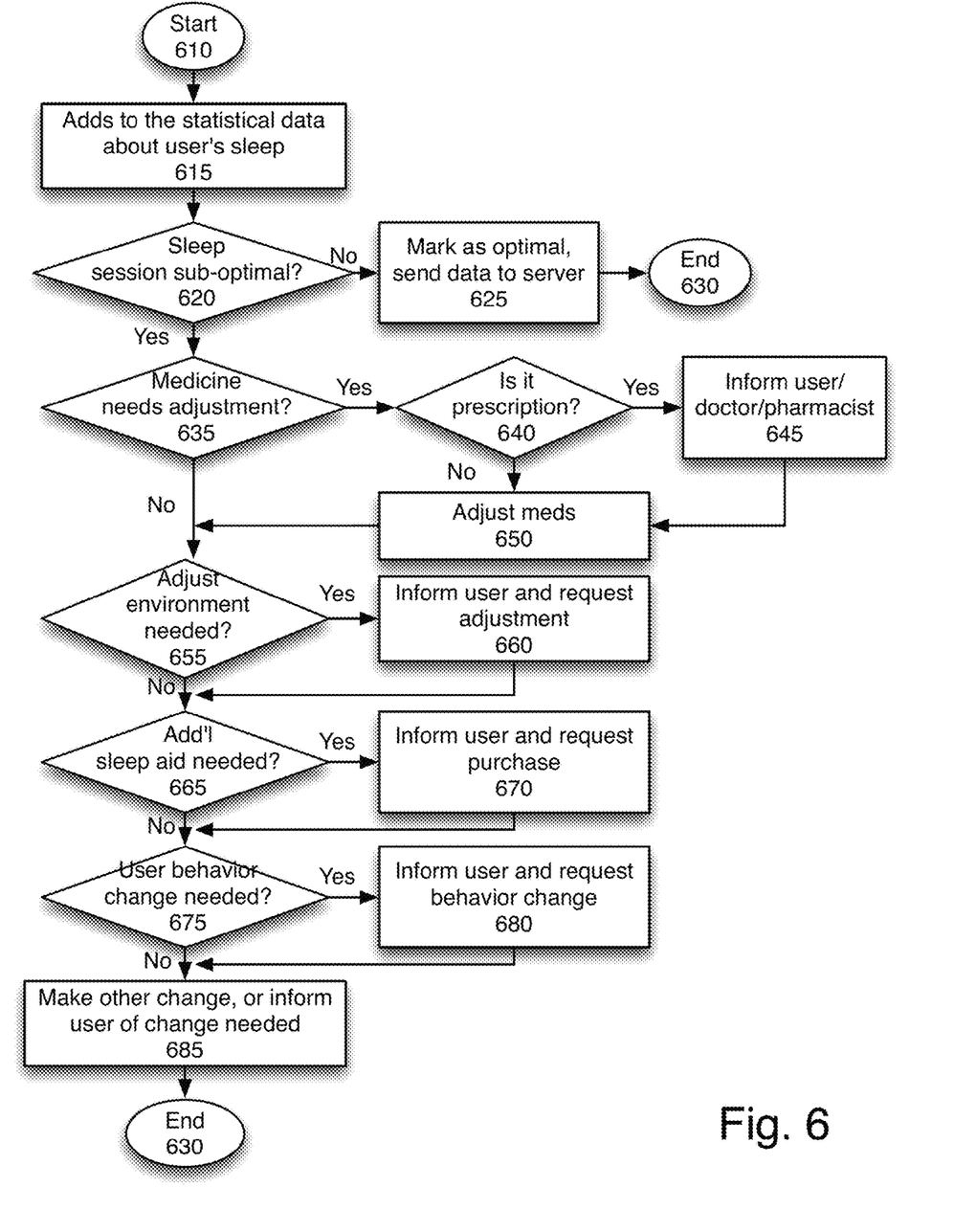
FIG. 6 is a flowchart of one embodiment of alerts utilized to adjust sleep aids based on analysis of the user's sleep.

FIG. 6 is a flowchart of one embodiment of alerts utilized to adjust sleep aids based on analysis of the user's sleep. The process starts at block 610.

At block 615, the process adds to the statistical data about the user's sleep patterns. In one embodiment, this may be done throughout a sleep session, or at the end of a sleep session.

At block 620, the process determines whether the sleep session was sub-optimal. Sub-optimal sleep sessions are those that are not sufficiently restful, too long for the level of refreshment achieved, or otherwise could be improved. If the sleep session was optimal, the process at block 625 sends the statistical data to the server/third party, as indicated by the user's settings. In one embodiment, the settings used for this sleep session are marked as having achieved optimal results. The process then ends at block 630. In one embodiment, the statistical data is also sent to third parties, such as the maker of one or more of the sleep aids. In one embodiment, the statistical data, anonymized, from multiple users may be utilized by the makers of the sleep aids to evaluate efficacy. In one embodiment, the user may opt into sharing this information with the maker of the sleep aid. In one embodiment, the user may be rewarded, financially or otherwise, for sharing his or her information.

If the sleeps session was suboptimal, the process at block 635 determines whether the medicine needs adjustment. Medicine may need adjustment due to timing (e.g. a time release medicine needs to be adjusted to provide a higher level of the medication in the early morning), dosage (too low or too high for optimum results), type (some people react negatively to particular medicines, and would do better with a similar but non-identical medication), or other adjustments. If the medicine needs adjustment, the process continues to block 640.

At block 640, the process determines whether the medicine is prescription. If so, in one embodiment the system at block 645 notifies the user, doctor, and/or pharmacist. In one embodiment, a user's prescription may be sufficiently flexible to allow a user to simply alter the medicine as needed. However, in most cases, changes to prescription medications are made with the cooperation of the user's doctor. At block 650, the medication is adjusted. If the medicine is not prescription, at block 650, the medication is adjusted, in one embodiment. In one embodiment, the medicine, in this context, may include non-drug medicines such as caffeine and alcohol intake. In on embodiment, adjusting the medications may include indicating to the user that he or she needs to stop drinking caffeine after 6 p.m., or drink a glass of wine, etc. In another embodiment, if the non-prescription medicine may be covered by insurance, the system may notify the user's doctor or insurer, or may indicate to the user how to do so.

The process then continues to block 655. If the medicine did not need adjustment, the process continues directly to block 655.

At block 655, the process determines whether an environmental adjustment is needed. Environmental adjustments may include changes in temperature, bedding, light levels, sounds, and other external conditions. When the system cannot automatically adjust these sleep aids, the user is requested to make the change. If such adjustments are needed, at block 660 the user is informed and requested to make the adjustment. The process then continues to block 665.

At block 665, the process determines additional sleep aids needed. Additional sleep aids may range from an eye mask to add darkness, to a positive airflow providing machine, or a white noise machine. When the system determines that a particular condition causes sleep disturbance, and the system cannot handle that disturbance given the existing conditions, a recommendation for additional sleep aids may be made. At block 670, the user is informed and purchase is requested. In one embodiment, the request may include a link to where the appropriate sleep aid can be purchased, enabling the user to complete the transaction quickly, and easily. In one embodiment, if such sleep aids are covered by insurance, the user is provided an easy process to apply for insurance coverage. In one embodiment, instead of notifying a user, a relevant entity—such as the user's guardian, doctor, or insurance company—may be notified. The process then continues to block 675.

At block 675, the process determines whether a user behavior change is needed. User behavior changes may include a change in activity timing, activity levels, food choices, or food levels, or additional behavioral changes. In one embodiment, the techniques in co-pending application Ser. No. 13/781,742 may be used to determine the needed changes. If such changes are needed, at block 680 the user is informed and requested to make the changes. The process then continues to block 685. At block 685, the user is prompted to make any other changes that need to be made. The process then ends at block 630.

Figure 7:
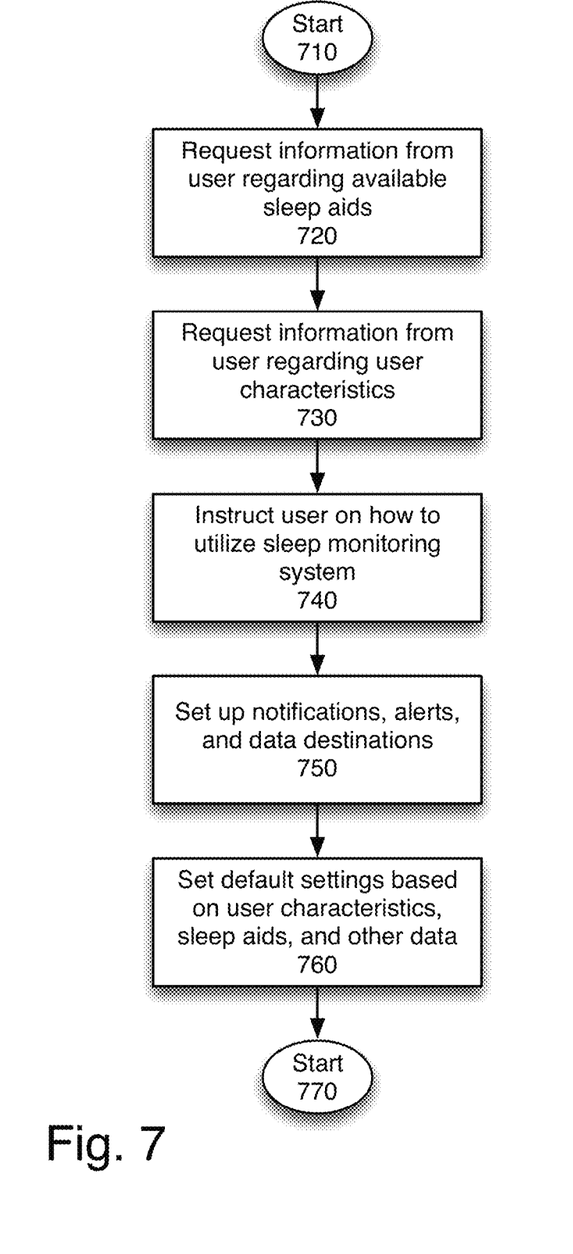
FIG. 7 is a flowchart of one embodiment of setting up the system.

FIG. 7 is a flowchart of one embodiment of setting up the system. The process starts at block 710. At block 720, the system requests information from the user regarding the available sleep aids. This may include medications, self-medicating non-prescription medicines, environmental controls, and other factors. In one embodiment, this may include a request to allow the system access to the relevant user medical records, to determine for example prescription sleep aid dosage.

At block 730, the process requests information from the user regarding the user's characteristics. The user's characteristics include the user's age, gender, health, and other relevant factors that may influence sleep requirements, and sleep quality. In one embodiment, this may include a request to allow the system access to the relevant user medical records.

At block 740, the system instructs the user on how to utilize the sleep monitoring system. This may include instructing the user to set up additional sleep aids, or now to set up controls that enable the monitoring system to interact with additional sleep aids.

At block 750, the system helps the user set up notifications, alerts, and data destinations. In one embodiment, notifications may be sent to the user, the user's doctor, a central database, or other locations. In one embodiment, the user may control how much or how little of the user's personal data is shared. In one embodiment, if the user is utilizing the system as part of a medical test or in another setting, these types of data sharing settings may be pre-set.

At block 760, the system sets the default settings for sleep aids as well as sleep needs, based on the above information. In one embodiment, each time user data is obtained, these default characteristics may be tweaked. For example, a default may be that most people sleep best if they are in bed by 11:30 p.m. and awake by 7:30 am. However, observed data may indicate that a particular user considers sleep most restful, and sleeps best when they go to bed at 2 a.m. and wake at 9 a.m. In that case, the system settings may be adjusted. In one embodiment, the default settings may be made available to the user, and adjusted by the user. The set-up then ends.

Figure 8:
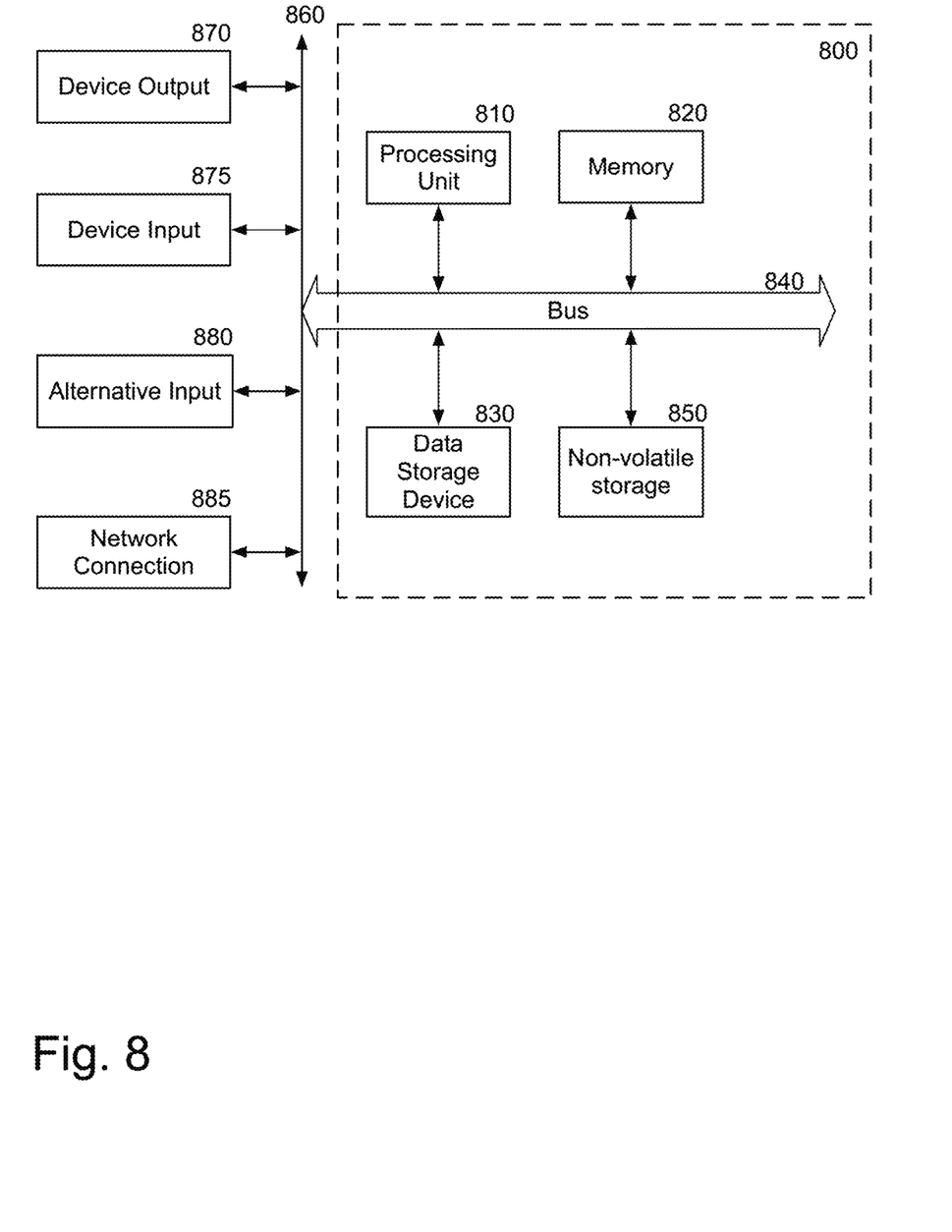
FIG. 8 is a block diagram of one embodiment of a computer system that may be used with the present invention.

FIG. 8 is a block diagram of one embodiment of a computer system that may be used with the present invention. FIG. 8 is a block diagram of a particular machine that may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment the system also includes a data storage device 830 such as a magnetic disk or optical disk and its corresponding disk drive, or Flash memory or other storage which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g., vibrations, etc.).

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, cellular network, wireless network or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine, which embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 840, the processor 810, and memory 820 and/or 850.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 810, a data storage device 830, a bus 840, and memory 820, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network connection 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

The invention claimed is:

1. A sleep aid system comprising a wearable device and a smartphone, wherein the wearable device is configured to:
   generate a user notification indicating it is time for a user to sleep;
   communicate the user notification to the smartphone through a wireless interface; and the smartphone is configured to:
   receive the user notification from the wearable device through the wireless interface;
   receive sleep data from the wearable device;
   prompt the user in response to receiving the user notification that indicates it is time for the user to sleep; and
   control the user's environment to both maintain the user in a current sleep state and transition the user to a next sleep stage.

2. The sleep aid system of claim 1, wherein the sleep aid system is configured to control the user's environment, including temperature, sounds, and light levels, for a sleep aid.

3. The sleep aid system of claim 1, wherein the sleep aid system is configured to play music for a sleep aid.

4. The sleep aid system of claim 1, wherein the sleep aid system interfaces with home automation controls.

5. The sleep aid system of claim 4, wherein the sleep aid system further interfaces with the home automation controls to adjust room light levels.

6. The sleep aid system of claim 1, further comprising an output device that is a visual output device, an audio output device, and/or tactile output device.

7. The sleep aid system of claim 6, wherein the output device is configured to wake up the user by vibrations and/or sounds.

8. A method to improve sleep aid user experience for a user utilizing a sleep aid, the method implemented by a sleep aid system comprising a wearable device and a smartphone, the method comprising:
   communicating a user notification to the smartphone through a wireless interface;
   receiving, by the smartphone, the user notification from the wearable device through the wireless interface;
   receiving, by the smartphone, sleep data from the wearable device;
   in response to the smartphone receiving the user notification, prompting the user that it is time for the user to sleep; and
   controlling, by the smartphone, the user's environment to both maintain the user in a current sleep state and transition the user to a next sleep stage.

9. The method of claim 8, further comprising controlling the user's environment, including temperature, sounds, and light levels for the sleep aid.

10. The method of claim 8, further comprising playing music for the sleep aid.

11. The method of claim 8, further comprising controlling to adjust room light levels by interfacing with home automation controls.

12. The method of claim 8, further comprising waking up the user by vibrations and/or sounds.

* * * * *